(12) United States Patent
Kobayashi

(10) Patent No.: US 6,916,761 B1
(45) Date of Patent: Jul. 12, 2005

(54) POLYMER-SUPPORTED LEWIS ACID CATALYST

(75) Inventor: Shu Kobayashi, Tokyo (JP)

(73) Assignee: Japan Science and Technology Corporation, Saitama (JP)

(*) Notice: Subject to any disclaimer, the term of this patent is extended or adjusted under 35 U.S.C. 154(b) by 400 days.

(21) Appl. No.: 09/889,406

(22) PCT Filed: Oct. 23, 2000

(86) PCT No.: PCT/JP00/07386
§ 371 (c)(1),
(2), (4) Date: Sep. 20, 2001

(87) PCT Pub. No.: WO01/36095
PCT Pub. Date: May 25, 2001

(30) Foreign Application Priority Data

Nov. 17, 1999 (JP) ............................................ 11-327424

(51) Int. Cl.[7] ........................... B01J 23/83; B01J 27/02; B01J 27/053; B01J 31/06; C08F 4/02
(52) U.S. Cl. ...................... 502/159; 502/102; 502/109; 502/122; 502/168; 502/216; 502/217; 502/302; 526/91
(58) Field of Search ................................ 502/159, 102, 502/107, 304, 122, 168, 216, 217, 219, 222, 223, 220, 302, 303, 402; 526/91

(56) References Cited

U.S. PATENT DOCUMENTS

| | | | | |
|---|---|---|---|---|
| 5,414,177 A | * | 5/1995 | Chung et al. ................ | 585/512 |
| 6,034,290 A | * | 3/2000 | Harmer et al. ............... | 570/236 |
| 6,197,715 B1 | * | 3/2001 | Bansleben et al. .......... | 502/155 |
| 6,281,309 B1 | * | 8/2001 | Babcock et al. ............. | 526/201 |

FOREIGN PATENT DOCUMENTS

| | | |
|---|---|---|
| JP | 9-262479 | 10/1997 |
| JP | 10-24234 | 1/1998 |
| JP | 10-230166 | 9/1998 |
| JP | 11-244705 | 9/1999 |

* cited by examiner

Primary Examiner—Michael La Villa
(74) Attorney, Agent, or Firm—Wenderoth, Lind & Ponack, L.L.P.

(57) ABSTRACT

In order to provide a novel Lewis acid catalyst, which shows high reaction activity in aqueous medium, is easily recovered, and is excellent in reusability, a Lewis acid group expressed by the general formula (I):

$$MX_n \qquad (I)$$

(wherein M represents a polyvalent element, X represents an anionic group, and n is an integer representing the valence of M) is linked and supported on a polymer membrane via an $SO_3$ or $SO_4$ group.

7 Claims, No Drawings

POLYMER-SUPPORTED LEWIS ACID CATALYST

TECHNICAL FIELD

The present invention relates to a polymer-supported Lewis acid catalyst. Particularly, the present invention relates to a novel Lewis acid catalyst, which shows high reactivity even in aqueous medium without the use of organic solvents, is easily prepared and recovered, and is excellent in reusability, and to methods of organic synthesis using such novel Lewis acid catalyst.

BACKGROUND ART

The execution of organic synthesis in aqueous medium without the use of harmful organic solvents has long been a major object in industry.

Heretofore, various methods of reaction in aqueous mediums containing organic solvent have been proposed, but none have been practical; one major reason being that in reactions performed in aqueous mediums, organic compounds are not soluble in water.

In order to solve such problems, the inventors of the present invention have developed Lewis acid-surfactant linked catalysts comprising scandium, tris(dodecylsulfate), scandium tris(dodecylsulfonate) or the like (Kobayashi, S., Wakabayashi, T., Tetrahedron Lett. 1998, 39, 5389; Kobayashi, S., Chem. Lett. 1991, 2187; Kobayashi, S., Nagayama, S., Busujima, T., J. Am. Chem. Soc. 1998, 120, 8287).

It has been said that by using such catalysts, organic compounds would quickly dissolve in water in a colloidal manner to allow reactions such as the aldol reaction of silyl enole ethers and aldehydes to proceed smoothly, without the use of organic solvents.

Although such substantial improvements were said to be possible, in reality, for the above catalyst, its recovery from water was not necessarily easy; hence, the difficulty in recovering and purifying the reaction products were problematic.

The invention of the present application has been achieved to solve the above-described problems, based on the knowledge on Lewis acid catalysts that enable organic synthesis in aqueous medium, proposed by the inventors, to provide a novel Lewis acid catalyst, which show high reaction activity in aqueous medium, may easily be recovered and is excellent in reusability.

DISCLOSURE OF INVENTION

In order to solve the above-described problem, the invention of the present application first provides a polymer-supported Lewis acid catalyst comprising a Lewis acid group expressed by the following general formula (I):

$$MX_n \quad (I)$$

(wherein M represents a polyvalent element, X represents an anionic group, and n is an integer representing the valence of M) linked and supported on a polymeric membrane via a $SO_3$ or $SO_4$ group.

Further, the invention of the present application secondly provides the above-described Lewis acid catalyst wherein the Lewis acid group of the following general formula (II):

$$—R^0\text{-}MX_n \quad (II)$$

(wherein M represents a polyvalent metallic element, X represents an anionic group, n is an integer representing the valence of M, and $R^0$ is a $SO_3$ or $SO_4$ group) is linked and supported on a polymeric chain via a spacer chain; provided thirdly, is the polymer-supported Lewis acid catalyst, wherein the spacer chain is a hydrocarbon group; provided fourthly, is the polymer-supported Lewis acid catalyst, wherein the spacer chain is expressed by the following general formula (III):

$$[(CH_2)_m Ph]_l \quad (III)$$

(wherein Ph represents a phenyl group and m and l each represent an integer of 1 or more).

Furthermore, the invention of the present application provides fifthly, any one of the above-described polymer-supported Lewis acid catalysts, wherein the polymer chain is a polymer obtained by the addition polymerization of an aromatic monomer; provided sixthly, is any one of the above-described polymer-supported Lewis acid catalysts wherein the polyvalent element (M) is a lanthanoid element.

Furthermore, the invention of the present application seventhly provides an organic synthesis reaction method using any one of the above-described polymer-supported Lewis acid catalysts, wherein the reaction is performed in water or an aqueous medium; and provided eighthly, is the above-described method of organic synthesis, comprising the formation of a carbon-carbon bond.

BEST MODE FOR CARRYING OUT THE INVENTION

In the Lewis acid catalyst of the present invention, a Lewis acid group expressed by the following general formula (I):

$$MX_n \quad (I)$$

is bonded to a polymeric chain. Here, the polyvalent element (M), which constitutes the Lewis acid group, may be chosen from various elements known conventionally to constitute a Lewis acid. For example, various types of elements such as Al, B, Ti, Zr, Sn, Zn, Ga, Bi, Sb, Si, Cd, V, Mo, W, Mn, Fe, Cu, Co, Pb, Ni, Ag, lanthanoid elements and so forth are illustrated. Among these elements, scandium (Sc), lanthanoid elements such as ytterbium (Yb) and lanthanum (La) are especially favorable in the present invention.

The anionic group (X) may be chosen from various types of anionic groups including those similar to conventional ones. For example, halogen atoms, organic acid groups and the like are included; as an organic acid group, for example, a sulfonic acid group such as trifluoromethane sulfonate (OTf), a phosphoric acid group and the like may be included.

In the present invention, such Lewis acid groups are linked to and supported on a polymeric membrane via a $SO_3$ (sulfonic acid) group or a $SO_4$ (sulfuric acid) group.

In such linkage, the polymeric chain or the molecular structure may comprise the direct bonding of the Lewis acid group to the polymeric chain via a $SO_3$ or $SO_4$ group, or the bonding of $SO_3$ or $SO_4$ group via a spacer molecular chain. In other words, the structure may be expressed by the following general formula (IV):

$$(A_1)\text{-}A_2—R^0\text{-}MX_n \quad (IV)$$

(wherein $R^0$ represents a $SO_3$ or $SO_4$ group, $A_1$ represents the polymer chain, and $A_2$ represents the spacer molecular chain)

Further, the $(A_2—R^0\text{-}MX_n)$ structure maybe in a state bonded to any desired number of polymer chains. The spacer chain may be constructed taking in consideration such points as the hydrophilic degree, productivity or a catalytic activity.

As the spacer chains, hydrocarbon groups may be illustrated as representative examples. Further, cycloalkyl groups and aryl groups may also be included. These hydrocarbon groups may optionally include substituents, as well. More specifically, as spacer molecular chains, those expressed by the following general formula (III):

$$[(CH_2)_mPh]_l \quad (III)$$

may be exemplified. Here, for example, m=1 to 7 and l=1 to 3 may be preferable.

The polymeric chain on which the Lewis acid catalyst is supported, may be chosen from various types; however, from the viewpoint of production and handling, polymers derived mainly from the addition polymerization of monomers are exemplified as favorable. Among them, aromatic addition polymerization monomers such as styrene, α-methylene, divinylbenzene and the like are illustrated.

In any of the above-described cases, the polymer chain used in the present invention is a solid substance insoluble in water or aqueous mediums.

As described above, the polymer-supported Lewis acid catalyst of the present invention maybe prepared, for example, by allowing the Lewis acid group to bond to a polymer chain or a polymer chain substance comprising a spacer molecular chain, via a $SO_3$ or $SO_4$ group. In such case, the $SO_3$ or $SO_4$ group may be bonded to the polymeric chain substance in advance, after which the Lewis acid group may be bonded to the $SO_3$ or $SO_4$ group, or the Lewis acid group having a $SO_3$ or $SO_4$ group may be bonded to the polymeric chain substance. Of course, the polymer-supported Lewis acid catalyst of the present invention is not limited to the above-described types, and maybe prepared by bonding a Lewis acid group to a polymer chain through various processes.

Further, the polymer-supported Lewis acid catalyst according to the present invention may be utilized in various types of organic synthesis reactions to exert the catalytic action of a Lewis acid. In such case, the reaction method is characteristic in that an aqueous medium, namely, water alone, may be used as the reaction medium. Of course, aqueous mediums obtained by mixing organic solvents such as alcohols, THF or other hydrophilic or polar solvents with water may be used; however, the most important characteristic of the polymer-supported Lewis acid catalyst of the present invention is that water alone may be used as the reaction medium, to obtain high reaction activity; further, the catalyst may easily be recovered because it is supported on solid polymer, and the high reaction activity is maintained even after recycling.

For the catalytic action of the Lewis acid catalyst, the polymer-supported Lewis acid catalyst of the present invention may be used effectively as the catalyst for, for example, alkylation reaction, allylation reaction, aldol-type reaction, Diels-Alder reaction, Strecker-type reaction and the like. In each of the above reactions, the reaction medium may be water or an aqueous medium.

Embodiments of the invention of the present application are described in more detail through the following examples.

EXAMPLES

Example 1

A polymer-supported scandium catalyst (A) was prepared as a polymer-supported Lewis acid catalyst of the present invention, according to the following reaction scheme:

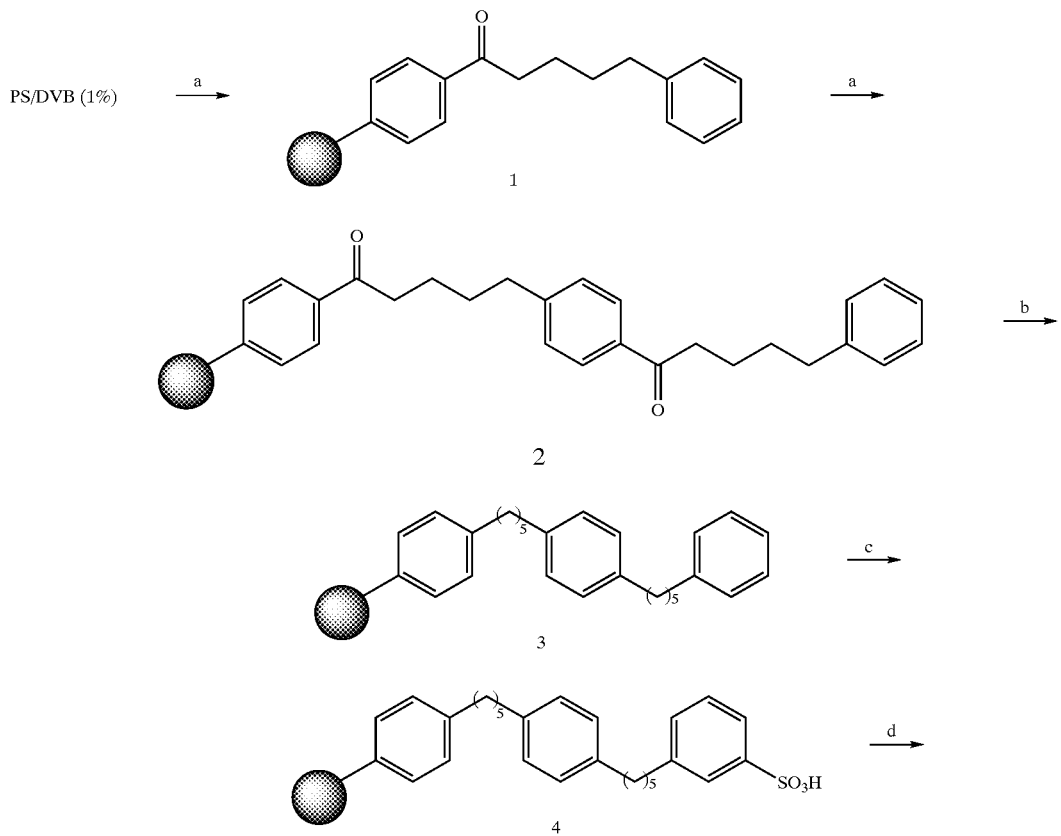

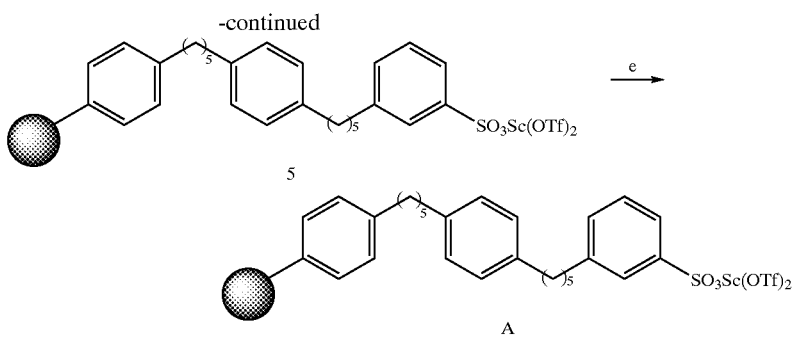

Namely, firstly, (a) polystyrene (5.0 g) cross-linked by 1% divinylbenzene (DVB) was reacted with 5-phenylvaleroylchloride (Ph(CH$_2$)$_4$COCl) (4.7 g; 24 mmol) in CS$_2$ (100 ml) in the presence of AlCl$_3$ (3.2 g, 24 mmol) at room temperature for 24 hours.

1N HCl (300 ml) was added to the resultant reaction mixture and stirred at the same temperature for 12 hours. Then, the mixture was filtrated, rinsed with H$_2$O, H$_2$O-THF, THF, and Et$_2$O, and then dried under reduced pressure; the ketonic reaction product (1) was obtained.

Identification results of compound (1) are shown in TABLE 1.

TABLE 1

$^{13}$C SR-MAS NMR (CDCl$_3$); δ = 24.1, 31.1, 35.8, 40.6, 125.7, 128.3, 128.6, 135.1, 142.2, 145.23, 199.8.
IR (neat) 1679 cm$^{-1}$.

Next, the ketonic product was reacted with 5-phenylvaleroylchloride (4.7 g, 24 mmol) in CS$_2$ (100 ml) in the presence of AlCl$_3$ (3.2 g, 24 mmol) and reacted under reflux for 24 hours. After the resultant reaction mixture was cooled to room temperature, 1N HCl (300 ml) was added and stirred for 12 hours. Then, the mixture was filtrated and rinsed with H$_2$O, H$_2$O-THF, THF, and Et$_2$O and thereafter, dried under reduced pressure; the diketone product (2) was obtained.

Identification results of compound (2) are shown in TABLE 2.

TABLE 2

$^{13}$C SR-MAS NMR (CDCl$_3$); δ = 24.0, 30.6, 31.1, 35.8, 38.1, 40.4, 125.7, 127.9, 128.3, 134.9, 142.2, 145.2, 199.8.
IR (neat) 1679 cm$^{-1}$.

(b) The diketone product (2) was reacted with AlCl$_3$ (6.4 g, 48 mmol)-LAH (1.9 g, 4.8 mmol) in ether (100 ml) under reflux condition for 12 hours. After the reaction mixture was cooled to 0° C., 1N HCl (300 ml) was added to the mixture and stirred for 12hours. Then, the stirred mixture was filtrated and rinsed with H$_2$O, H$_2$O-THF, and THF, and thereafter, dried under reduced pressure; the reduction product (3) was obtained.

Identification results thereof are as follows:

TABLE 3

$^{13}$C SR-MAS NMR (CDCl$_3$); δ = 24.8, 29.0, 31.3, 35.5, 35.9, 40.4, 125.7, 128.2, 139.9, 142.7, 145.5.

(c) The reduction product (3) was reacted with chlorosulfonic acid: ClSO$_3$H (0.47 g, 4.0 mmol) in dichloromethane (25 ml) at 0° C. for 12 hours. Then, acetic acid (25 ml) was added to the resultant reaction mixture to terminate the sulfonation reaction. The resultant reaction mixture was filtrated then rinsed with H$_2$O, H$_2$O-THF, THF, and Et$_2$O, and thereafter, dried under reduced pressure; the sulfonic acid product (4) was obtained. The supported amount of compound (4) was confirmed to be 1.29 mmol/g, through acid-base titration. Further, the identification result thereof was IR (neat) 1679 cm$^{-1}$.

(d) The sulfonic acid product (4) (1.0 g) was reacted with scandium chloride: ScCl$_3$.6H$_2$O (370.1 mg) in acetonitrile (10 ml) under reflux for 24 hours. After the resultant reaction mixture was cooled to room temperature, acetonitrile (10 ml) was added, after which the mixture was filtrated and rinsed with acetonitrile, and dried under reduced pressure; the scandium-bonded product (5) was obtained.

(e) The scandium-bonded product (5) was reacted with trifluoromethane sulfonic acid: T$_f$OH (186.7 mg, 1.24 mmol) in dichloromethane (10 ml) at room temperature for 12 hours.

Water (10 ml) was added to the resultant reaction mixture, which was then filtrated, rinsed with H$_2$O, H$_2$O-THF, THF, and Et$_2$O, and thereafter, dried under reduced pressure; the polymer-supported scandium catalyst (A) was obtained.

Elemental analysis, confirmed the presence of 0.6% of scandium.

Example 2

Using the catalyst (A) obtained in Example 1, the allylation reaction of 4-phenyl-2-butanone with tetraallyltin was performed, according to the following reaction scheme:

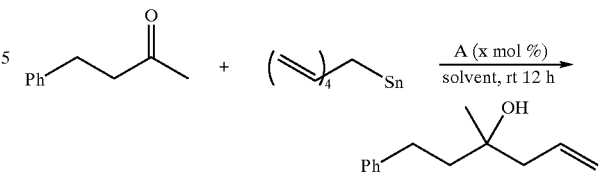

The reaction was performed in various media including water, at room temperature for 12 hours. In such reaction, 4-phenyl-2-butanone (0.4 mmol) and tetraallyltin (0.2 mmol) were used with a predetermined amount of the catalyst (A). 3 ml of a solvent was used therein. The reaction results are shown in TABLE 4.

TABLE 4

| Conditions | Solvents | Catalysts (mol %)[a] | Yields (%) |
|---|---|---|---|
| 1 | H₂O | 3.2 | 92 (93[b], 90[c]) |
| 2 | H₂O | 1.6 | 95 (90[d], 92[e]) |
| 3 | H₂O | 0.8 | 84 |
| 4 | CH₂Cl₂ | 3.2 | 38 |
| 5 | CH₃CN | 3.2 | 15 |
| 6 | Benzene | 3.2 | 28 |
| 7 | EtOH | 3.2 | 20 |
| 8 | DMF | 3.2 | trace |

*Unless otherwise specified, compound 5 (1.29 mmol/g) was used.
[a] determined by elemental analysis of scandium in compound 1
[b] reused (second time)
[c] reused (third time)
[d] compound 5 (0.52 mmol/g) used
[e] compound 5 (2.46 mmol/g) used.

In the reaction wherein water was used as the reaction medium and 3.2 mol % of the polymer-supported scandium catalyst (A) was used (condition 1), a homoallylalcohol compound was obtained in a high yield of 92%. On the other hand, reactions wherein organic solvents were used (conditions 4 to 8) showed low reaction yield.

Further, with condition 1, even when the catalyst (A) was reused for the second time and, moreover, for the third time, high reaction yields of 93% and 90% were obtained, respectively. The process of recovering the catalyst (A) was easy, and only involved filtration.

In addition, in condition 2, a high yield of 95% was obtained by using 1.6 mol % of the catalyst (A).

Example 3

As in Example 2, the allylation of various types of aldehyde compounds and ketone compounds were performed in an aqueous medium according to the following reaction scheme:

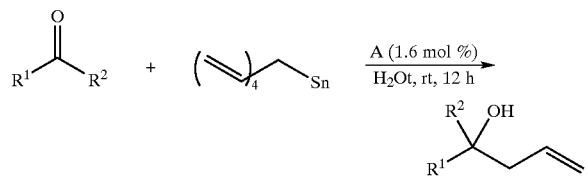

The reactions were carried out using 1.6 mol % of the above-described catalyst (A) at room temperature for 12 hours. Results are shown in TABLE 5.

TABLE 5

| Conditions | R¹ | R² | Yields (%) |
|---|---|---|---|
| 1 | Ph | H | 82 |
| 2 | Ph(CH₂)₂ | H | quant |
| 3 | c-C₅H₁₁ | H | 72 |
| 4 | (E)-PhCH=CH | H | 99 |
| 5 | 2-pyridyl | H | 83 |
| 6 | PhCO | H[a] | 90[b] |
| 7 | Ph(CH₂)₂ | Me | quant |
| 8 | (E)-PhCH=CH | Me | 91 |
| 9 | Ph | CO₂Et | 90 |

[a] Monohydrate
[b] diallylation product obtained

Each reaction showed a high yield.

Example 4

Using 3.2 mmol % of the above-described polymer-supported scandium catalyst (A), benzaldehyde and 1-ethylthio-1-trimethylsiloxy-2-methylpropane were reacted in 5 ml of aqueous medium at room temperature for 12 hours according to the following reaction scheme:

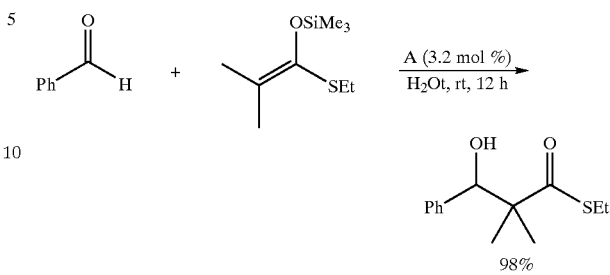

As a result, the corresponding aldol-type reaction product was obtained in a high yield of 98%.

When the amount of catalyst (A) was decreased to 1.6 mol %, the yield was 77%.

Identification results of the product, S-ethyl-3-hydroxy-2,2-dimethyl-3-phenylpropanethioate, are shown in TABLE 6.

TABLE 6

S-Ethyl-3-hydroxy-2,2-dimethyl-3-phenylpropanethioate

¹H NMR (CDCl₃); d = 1.05 (s, 3H), 1.15 (s, 3H), 1.18 (t, 3H, 7.4 Hz), 2.81 (q, 2H, 7.4 Hz), 2.90 (br, 1H), 4.87 (s, 1H), 7.19–7.25 (m, 5H).
¹³C NMR (CDCl₃); d = 14.4, 20.0, 23.3, 23.6, 54.3, 78.9, 127.7, 127.8, 139.9, 207.9.

Example 5

As in Example 1, a polymer-supported ytterbium catalyst was prepared, using ytterbium (Yb) instead of scandium, and used in a reaction similar to that of Example 4. The reaction performance obtained was approximately equivalent to that obtained for Example 4.

Example 6

Using 1.6 mol % of the above-described catalyst (A), the Diels-Alder reaction of 3-acroxy-1,3-oxazolidine-2-one and cyclopentadiene was performed in an aqueous medium at room temperature for 12 hours according to the following reaction scheme:

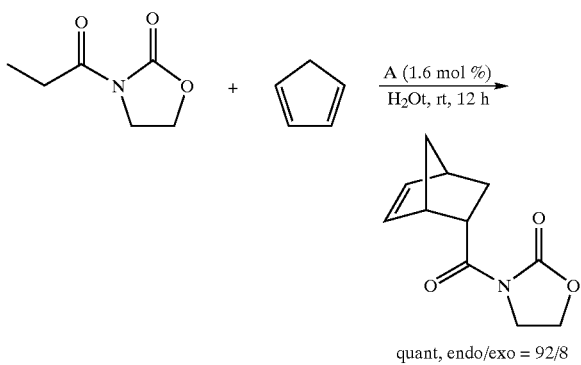

The adduct: 3-(bicyclo[2,2,1]hepta-5-ene-2-yl-1,3-oxazolidine-2-one was obtained quantitatively (endo/exo= 92/8) as the reaction product.

Example 7

Using 1.6 mol % of the above-described catalyst (A), a Strecker-type reaction of benzaldehyde, aniline, and tributyltincyanide was performed in an aqueous medium according to the following reaction scheme. The reaction was carried out at room temperature for 12 hours.

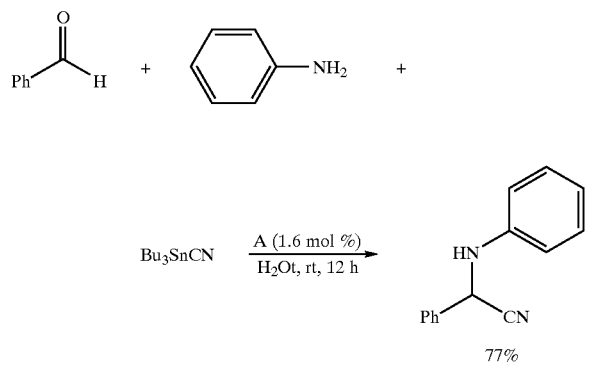

The corresponding α-aminonitrile; 1-phenyl-1-phenylaminonitrile was obtained in a 77% yield.

Identification results thereof are shown in TABLE 7.

TABLE 7

| 1-Phenyl-1-phenylaminonitrile |
|---|
| $^1$H NMR (CDCl$_3$); d = 4.20 (d, 1H, J. = 9.23 Hz), 5.61 (d, 1H, J. = 9.24 Hz), 6.75–6.78 (m, 2H), 6.88–7.00 (m, 2H), 7.22–7.36 (m, 6H).<br>$^{13}$C NMR (CDCl$_3$); d = 46.04, 104.5, 114.5, 117.5, 126.7, 127.1, 127.2, 129.5, 136.7, 144.0. |

INDUSTRIAL APPLICABILITY

As described above in detail, the invention of the present application provides a novel Lewis acid catalyst, which shows high reaction activity in aqueous medium, is easily recovered, and is excellent in reusability, as well as a method of organic synthesis using such novel catalyst.

What is claimed is:

1. The polymer-supported Lewis acid catalyst comprising a Lewis acid group expressed by the following general formula (II):

$$—R^0\text{-}MX_{n-1} \tag{II}$$

wherein M represents a lanthanoid element, X represents an anionic group, n is an integer representing the valence of M, and $R^0$ represents a $SO_3$ or $SO_4$ group, said Lewis acid group being bonded to a polymeric chain via a spacer chain, wherein the spacer chain is a hydrocarbon group.

2. A polymer-supported Lewis acid catalyst comprising a Lewis acid group expressed by the following general formula (II):

$$—R^0\text{-}MX_{n-1} \tag{II}$$

wherein M represents a lanthanoid element, X represents an anionic group, n is an integer representing the valence of M, and $R^0$ represents a $SO_3$ or $SO_4$ group, said Lewis acid group being bonded to a polymeric chain via a spacer chain, wherein the spacer chain is expressed by the following general formula (III):

$$[(CH_2)_m Ph]_l \tag{III}$$

wherein Ph represents a phenyl group, and m and l each represent an integer greater than or equal to 1.

3. The polymer-supported Lewis acid catalyst of claim 1 or 2, wherein the polymeric chain comprises a polymer obtained by the addition polymerization of aromatic monomers.

4. A method of organic synthesis which comprises conducting an organic reaction using the polymer-supported Lewis acid catalyst of claim 1 or 2, wherein the reaction is performed in water or an aqueous medium.

5. The method of organic synthesis according to claim 4, which comprises the formation of a carbon-carbon bond.

6. The polymer-supported Lewis acid catalyst of claims 1 or 2, wherein X is a halogen atom or an organic acid group.

7. The polymer-supported Lewis acid catalyst of claims 1 or 2, wherein X is a perfluoroalkyl sulfonate group.

* * * * *